United States Patent [19]
Hassler et al.

[11] Patent Number: 5,309,897
[45] Date of Patent: May 10, 1994

[54] APPARATUS FOR GENERATING ACOUSTIC RAREFACTION PULSES

[75] Inventors: Dietrich Hassler, Uttenreuth; Helmut Reichenberger, Eckental; Hubert Schwark, Buckenhof; Georg Koehler, Geisfeld, all of Fed. Rep. of Germany

[73] Assignee: Siemens Aktiengesellschaft, Munich

[21] Appl. No.: 739,179

[22] Filed: Aug. 1, 1991

[30] Foreign Application Priority Data

Aug. 2, 1990 [EP] European Pat. Off. ........ 90114880.9

[51] Int. Cl.$^5$ .............................................. A61B 17/22
[52] U.S. Cl. ................................... 601/4; 128/660.03
[58] Field of Search ........ 128/24 AA, 24 EL, 660.01, 128/660.03; 73/624, 625, 627-629

[56] References Cited

U.S. PATENT DOCUMENTS

| | | |
|---|---|---|
| 4,194,510 | 3/1980 | Proudian . |
| 4,622,969 | 11/1986 | Forssmann et al. ............ 128/24 EL |
| 4,697,588 | 10/1987 | Reichenberger . |
| 4,721,108 | 1/1988 | Heine et al. ..................... 128/24 EL |
| 4,972,826 | 11/1990 | Koehler et al. ................. 128/24 EL |
| 5,058,569 | 10/1991 | Hassler et al. .................. 128/24 EL |

FOREIGN PATENT DOCUMENTS 0330816 1/1989 European Pat. Off. .
1572400 3/1970 Fed. Rep. of Germany .

OTHER PUBLICATIONS

"Stosswellen in der Medizon" Forsmann et al., Medizin unserer Zeit, vol. 4, No. 1, 1980 pp. 10-14.

Primary Examiner—Lee S. Cohen
Assistant Examiner—K. M. Pfaffle
Attorney, Agent, or Firm—Hill, Steadman & Simpson

[57] ABSTRACT

An apparatus for generating acoustic rarefaction pulses, i.e., a negative pressure pulse, has a pressure pulse source and reflector having a negative reflection factor, and an acoustic propagation medium filling the space between the pressure pulse source and the reflector. The reflector has a boundary surface facing toward the pressure pulse source, consisting of a medium which is acoustically soft in comparison to the acoustic propagation medium. The boundary surface medium is separated from the acoustic propagation medium by a wall which is impenetrable by the acoustic propagation medium.

13 Claims, 3 Drawing Sheets

APPARATUS FOR GENERATING ACOUSTIC RAREFACTION PULSES

BACKGROUND OF THE INVENTION

1. Field of the Invention

The present invention is directed to a generator for generating acoustic traction pulses having a pressure pulse source, a reflector having a negative reflection factor and an acoustic propagation medium filling out at least the space between the pressure pulse source and the reflector.

2. Description of the Prior Art

Medical therapy devices are known which generate a negative pressure pulse, commonly referred to as a rarefaction or tensile pulse, wherein an inversion of the operational sign of the pressure pulse incident into the reflector, and emanating positive from the pressure pulse source, occurs given reflection at a reflector having a negative reflection factor. The term "pressure pulse" shall be employed below exclusively for pressure pulses having a positive operational sign. Generators that are capable of generating rarefaction pulses are employed for treating pathological tissue modifications, for example tumors. There are indications that the cavitation phenomena in the pathological tissue occurring due to irradiation with rarefaction pulses lead to cell damage that at least opposes the further spread of the pathological tissue modifications.

German OS 38 06 532 discloses a generator of this type, however, no details are provided about the structure of the reflector having a negative reflection factor. Such generators have been tested with reflectors formed of a foamed material having closed pores. As a result of the gas enclosed in the pores, such foams are acoustically softer than the standard propagation media, which are usually liquid. As a consequence of the fact that the material of the reflector is acoustically softer than the acoustic propagation medium, i.e. has a characteristic acoustic impedance that is lower than that of the acoustic propagation medium, there is a negative reflection factor between the acoustic propagation medium and the reflector. Pressure pulses incident into the reflector are thus reflected as rarefaction pulses. The tested generators were in fact fundamentally functional; however, there is a risk that the pore walls of the foamed material will become perforated if subjected to the influence of pressure pulses over a longer period of time. This results in the liquid acoustic propagation medium penetrating into the formed material so that the reflector and thus the generator, can no longer function as desired. There is also the risk that liquid acoustic propagation medium will slowly diffuse into the foamed material, likewise leading to a malfunction of the generator.

SUMMARY OF THE INVENTION

An object of the present invention is to provide a rarefaction pulse generator which has a high service life.

This object is achieved in accordance with the principles of the present invention in a generator wherein the reflector has a boundary surface of a medium that is acoustically soft in comparison to the acoustic propagation medium, this boundary surface facing toward the pressure pulse source and being separated from the acoustic propagation medium by a wall which is impenetrable by the acoustic propagation medium. It is thus assured that penetration of the acoustic propagation medium behind the wall will not occur even when the influence of the pressure pulses produces mechanical modifications at the acoustically soft medium. Failure of the generator due to a failure of the reflector is thus avoided. Further, the presence of the wall creates the possibility of using not only foamed materials, but virtually any arbitrary acoustically soft media.

A preferred embodiment of the invention uses a gaseous medium as the acoustically soft medium. The gaseous medium is enclosed, for example, in a space that has its surface facing toward the pressure pulse source closed by the wall. There is also the possibility of providing an expanded polymeric material (foamed material) as the acoustically soft medium. This material need not necessarily have closed pores, however, it is separated from the acoustic propagation medium by the wall. For geometrically faultless reflection properties, surface roughness and other shape deviations of the boundary surface from its ideal shape must be significantly below (approximately 10 times below) the wavelength of the pressure pulses incident into the reflector. A boundary surface fashioned in this manner is referred to below as being smooth.

To prevent the presence of a wall having disadvantageous effects on the reflection behavior of the reflector, in a further embodiment of the invention the wall is fashioned of a material whose acoustic impedance essentially corresponds to that of the acoustic propagation medium. This assures that reflections do not first occur at the boundary surface between the acoustic propagation medium and the wall, but instead occur first at the boundary surface of the acoustically soft medium. Disturbing influences as a consequence of the wall can also be avoided if this is formed of a material that is acoustically hard in comparison to the acoustic propagation medium, i.e. has a higher acoustic impedance, whereby the wall has a thickness that is low (for example, ten times less) in comparison to the wavelength of the pressure pulses in the material of the wall. Because the wall is thin in comparison to the wavelength, the pressure pulses do not "notice"/the intrinsically higher characteristic impedance of the wall material, and the boundary layer to the acoustically soft medium defines the reflection behavior.

If expanded polymeric material is used as the acoustically soft medium, in another embodiment of the invention the wall is joined to the surface of the expanded polymeric material such that it forms the boundary surface, so that the expanded material is sealed at least liquid-tight, preferably gas-tight and liquid-tight if a liquid acoustic propagation medium is used. For example, this can be achieved by gluing a thin metal or plastic foil to the boundary surface, or the expanded polymeric material in the region of the boundary surface may be fused to form a tight wall by applying heat.

In another embodiment of the invention also employing an expanded polymeric material as the acoustically soft medium, has the aforementioned wall formed of a non-expanded layer of polymeric material, whereby the thickness of the layer is small in comparison to the wavelength of the pressure pulses in the non-expanded polymeric material. The non-expanded layer can be joined to the expanded polymeric material to form a one-piece component, this being easily achievable on the basis of suitable, known manufacturing methods.

Focusing means, if used, can be expediently arranged between the pressure pulse source and the reflector in a further embodiment of the invention. A planar reflector that can be simply and economically manufactured can then be employed. In another embodiment of the invention, however, there is also the possibility of forming the focusing means with the appropriately-shaped boundary surface of the acoustically soft medium. This has the advantage that the outlay for special focusing means, for example acoustic lenses, etc., is eliminated. It is also possible to reflect unfocused pressure pulses as rarefaction pulses with a planar reflector in that the traction pulses proceed to focusing means, which then supply focused rarefaction pulses.

DESCRIPTION OF THE PREFERRED EMBODIMENTS

Figure 1:
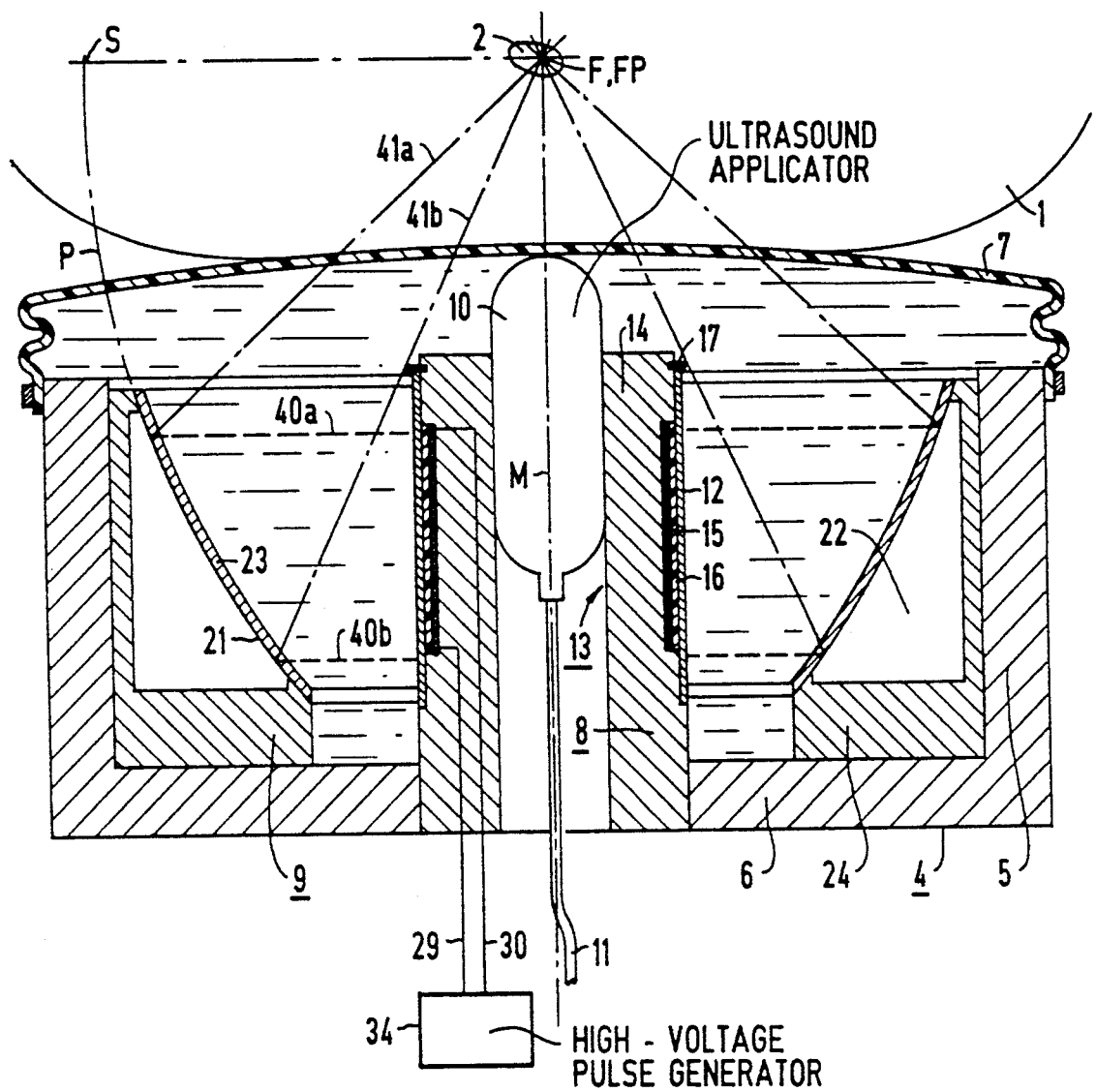
FIG. 1 is a schematic illustration of a longitudinal section through an acoustic generator constructed in accordance with the principles of the present invention.

An acoustic generator of the invention shown in FIG. 1 serves the purpose of irradiating pathological tissue modifications 2 situated in a body of a patient 1 schematically indicated in cross section.

The generator has a housing 4 formed by a cylindrical tubular wall section 5 and a base 6. At its end lying opposite the base 6, the housing 4 is closed with a flexible bellows 7 that serves the purpose of pressing the generator—as shown—against the body of the patient 1 for acoustic coupling. The interior of the housing 4 closed by the bellows 7 contains a liquid acoustic propagation medium, for example water.

A pressure pulse source generally referenced 8, a reflector 9 and an ultrasound transducer 10 are arranged in the inside of the housing 4. The pressure pulse source 8 and the reflector 9 serve the purpose of generating focused rarefaction pulses in the propagation medium that converge in a focus zone F. The ultrasound transducer 10 is a component of an ultrasound locating system that serves the purpose of aligning the generator relative to the body of the patient 1 so that the tissue modification 2 to be treated is situated in the focus zone F of the rarefaction pulses. The ultrasound transducer 10 is connected via a cable 11 to ultrasound control and imaging electronics (not shown) for producing, preferably, ultrasound B-images in known way. These images represent a body slice of the patient 1 containing the center axis M of the generator, this body slice containing the focus zone F lying on the center axis M.

The pressure pulse source 8 has an essentially hollow-cylindrical membrane 12 consisting of electrically conductive material, for example copper, that is tubularly fashioned. A coil arrangement 13 has a cylindrically helical coil 15 wound onto an approximately cylindrical coil carrier 14 formed of an electrically insulating material. The coil arrangement is situated inside the membrane 12. To avoid voltage arcing between the coil 15 and the membrane 12, the coil 15 has its outer surface completely surrounded by an insulating foil 16, whose thickness, is shown exaggerated in FIG. 1 (as are the thicknesses of the membrane 12 and of the coil 15).

The coil 15 and the insulating foil 16 are accepted in an annular recessed portion of the coil carrier 14. The membrane 12 has a larger length than the coil 15 and is placed onto the coil carrier 14 free of radial play such that it projects beyond the coil 15 at both sides. The membrane 12 is fixed axially non-dislocatable between a snap ring 17 and a shoulder of the coil carrier 14. The space between the membrane 12 and the coil 15 or the insulating foil 16 can be charged with sub-atmosphere pressure in a way that is not shown, as is known from U.S. Pat. No. 4,697,588 for a planar membrane.

One end of the coil carrier 14 is fixed in a corresponding bore of the base 6 of the housing 4. An approximately tubularly rotationally symmetric reflector 9 in the housing 4 that surrounds the pressure pulse source 8 and has a concave reflector face 21 facing toward the pressure pulse source 8. The reflector face 21 is obtained by the rotation of a segment of a parabola P (indicated dot-dashed in FIG. 1) around the center axis M of the generator, whereby the focal point FP of the parabola P corresponds to the center point of the focus zone F and lies on the center axis M of the generator, and the vertex S of the parabola P lies on a straight line that intersects the center axis M of the generator at a right angle. The center axis M of the generator corresponds to the center axis of the reflector face 21. The reflector 9 and the pressure pulse source 8 are arranged relative to one another so that the respective center axes of the reflector face 21 and of the membrane 12 coincide.

In the generator of the invention, the reflector face 21 is formed by a smooth boundary surface—facing toward the membrane 12—of a volume 22 of a gaseous medium, for example air, that is acoustically soft in comparison to the water provided as the acoustic propagation medium. The air volume 22 is separated from the water provided as the acoustic propagation medium by a wall 23 that is formed of a material, for example sheet brass, that is resistant to pressure pulses. The wall 23 is formed, for example, by deep drawing. The thickness of the wall 23 is selected such that it is small (for example, 5 through 10 times smaller) in comparison to the wavelength of the pressure pulses in the material of the wall 23. The wall 23 is soldered gas-tight and liquid-tight to a ring 24 having an approximately L-shaped cross section that has its respective legs pressing against the wall section 5 and the base 6 of the housing 4.

The terminals 29 and 30 (only schematically indicated) of the coil 15 are conducted in a manner not shown in detail to that end of the coil carrier 14 in the base 6 of the housing 4, through bores proceeding in the coil carrier 14 in the direction of the center axis M. As is the cable 11, the terminals 29 and 30 are conducted liquid-light through the base 6 of the housing 4 toward the exterior in a manner not shown in detail, and are connected to a high-voltage pulse generator 34.

The functioning of the described generator is as follows:

When the coil arrangement 13 is charged with a high-voltage pulse by the high-voltage pulse generator 34, this causes the coil arrangement 13 to construct a magnetic field extremely quickly. As a result a current is simultaneously induced in the membrane 12, this current being opposite the current flowing in the coil arrangement 13 and, consequently, generating an opposing magnetic field. The membrane 12 is suddenly repelled from the coil arrangement 13 under the influence thereof. As a result a radially outwardly expanding pressure pulse in the shape of a cylindrical wave is generated by the membrane 12 in the acoustic propagation medium that adjoins the outside of the membrane 12.

The cylindrical wave pressure pulse emanating from the membrane 12 whose boundary rays 40a, and 40b are indicated with broken lines in FIG. 1, is incident on the reflector face 21 of the reflector 9. As indicated by the broken-line boundary rays 41a and 41b, this wave is reflected such therefrom such that it converges in the focus zone F whose center point corresponds to the focal point FP of the parabola P. Because the reflector face 21 is a boundary surface of a medium, namely air, that is acoustically soft in comparison to the water provided as the acoustic propagation medium, the pressure pulse is reflected at the boundary surface formed by the reflector face 21 as a rarefaction pulse. Regardless of the fact that the boundary surface of the air volume 22 is separated from the water provided as the acoustic propagation medium by the wall 23, which has a high acoustic impedance in comparison to the two propagation media, i.e. is acoustically hard, there is a negative reflection factor for the pressure pulses incident into the reflector 9. Because the thickness of the wall 23 is small in comparison to the wavelength of the pressure pulses in the material of the wall 23, the pressure pulses are not affected by the wall 23. Despite the non-linear compression properties of water, the pressure pulses incident on the reflector 9, given an electromagnetic pressure pulse source as set forth above, are usually only insignificantly steepened and have a wavelength on the order of magnitude of 15 mm, so that it is possible without difficulty to execute the wall 23 with an adequate thickness. Even when the propagation distance of the pressure pulses present between the pressure pulse source 8 and the reflector face 21 is large enough so that these pressure pulses steepened into shock waves, it is usually possible in practice to provide an adequately thin wall 23.

When treating a patient 1, the generator is first aligned relative to the body of the patient 1 using the ultrasound locating system such that the tissue modification 2 to be irradiated lies on the center axis M of the generator. The depth of the calculus 2 in the body of the patient 1 can now be seen. Corresponding to the respective depth, the generator is then shifted in the direction of its center axis M until the tissue zone 2 to be treated is situated in the focus zone F. The tissue zone 2 is now charged with a series of rarefaction pulses.

Figure 2:
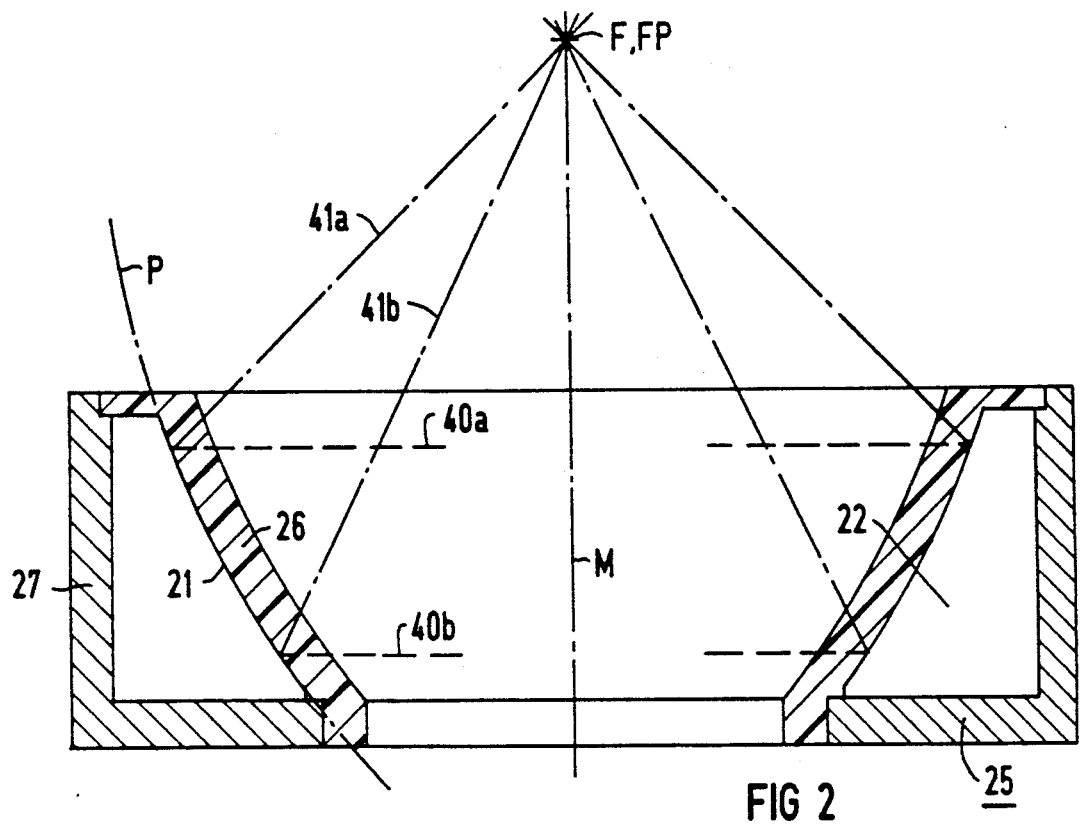
FIGS. 2 and 3 are respective schematic illustrations of longitudinal sections through different embodiments of the reflector of the generator of FIG. 1.

FIG. 2 shows a reflector 25 that can be utilized in the generator of FIG. 1 instead of the reflector 9. The reflector 25 differs from that set forth above in that the wall 26 separating the air volume 22 from the acoustic propagation medium at the boundary surface 21 is composed of material whose acoustic impedance is essentially the same as that of the acoustic propagation medium. If water is employed as the acoustic propagation medium, polymethylpenten (TPX) is suitable as the material for the wall 26. As a consequence of the fact that the acoustic impedances of the material of the wall 26 and of the acoustic propagation medium as essentially identical, no noteworthy reflections occur at the boundary surface between the wall 26 and the acoustic propagation medium since the reflection factor is extremely low. Reflections first occur at the boundary surface 21, where a negative reflection factor is again present here. Since the acoustic impedances of the material of the wall 26 and of the acoustic propagation medium are essentially the same, there is no absolute necessity to make the wall 26 especially thin. The wall 26 is again connected gas-tight and liquid-tight to a ring 27 having an approximately L-shaped cross section. Due to the different sound propagation speeds in water (approximately 1500 m/s) and in TPX (approximately 200 m/s), refraction phenomena occur at the boundary surface of the wall 26 to the acoustic propagation medium and these refraction phenomena, dependent on the wall thickness, may have to be taken into consideration under certain circumstances in such a way that the reflector face 21 has a shape deviating slightly from the parabola shape.

Figure 3:
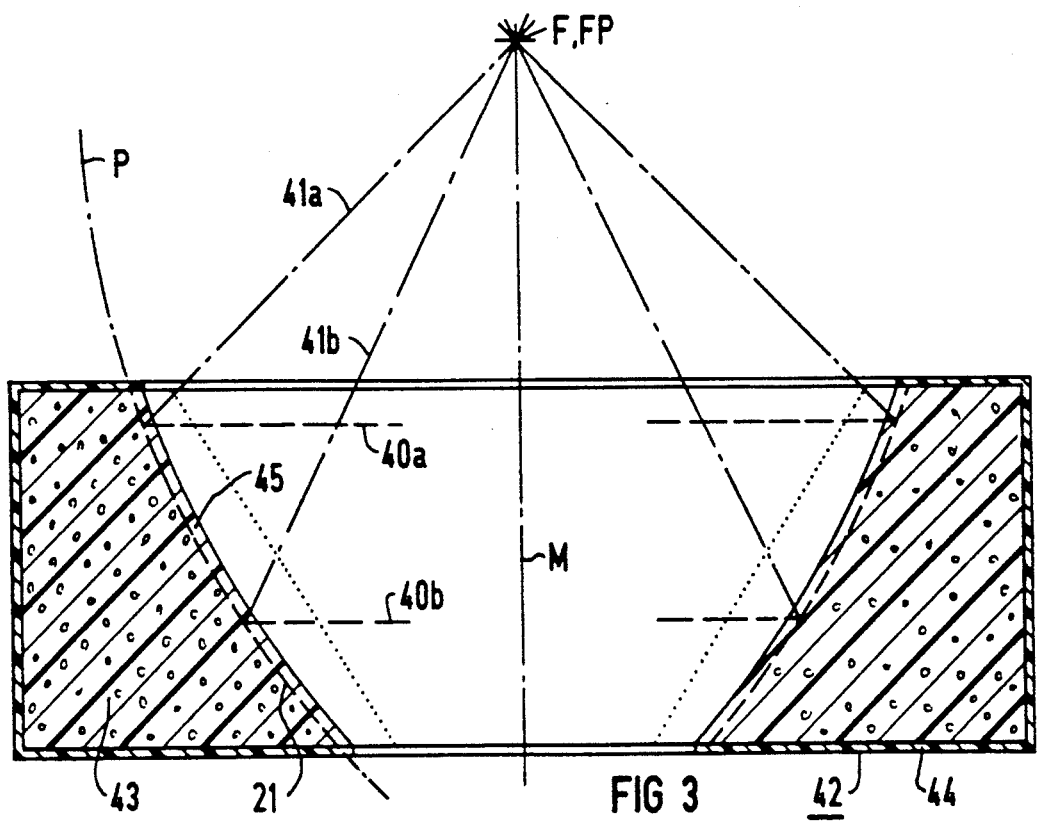

A further embodiment of a reflector 42 suitable for the generator of FIG. 1 is shown in FIG. 3. In the case of this reflector, expanded polymeric material 43 is provided as the acoustically soft medium, which simultaneously forms the base member of the reflector 42. The expanded polymeric material can, for example, by Styropor ® or polyurethane foam. In order to protect the expanded polymeric material against injurious influences, the reflector 42—except its surface facing toward the center axis M the pressure pulse source—is sealed with a plastic foil 44 that is joined to the expanded polymeric material 43, for example by gluing. The smooth boundary layer 21 of the expanded polymeric material 43 provided as the acoustically soft medium is separated from the acoustic propagation medium by a closed, pore-free wall 45 that is formed by a region of the polymeric material wherein the polymeric material is not expanded. Within the present application, the term "not expanded" means that the polymeric material has a non-foamed structure. Polymeric material initially present in the non-expanded region as a foamed structure can be converted into a non-foamed structure by known suitable measures or the creation of a foamed structure in the non-expanded region can be avoided from the beginning with known measures when expanding the polymeric material. In both instances, the non-expanded region of the polymeric material forming the wall 45 is connected to form a one-piece component with the expanded polymeric material 43 provided as the acoustically soft medium, this being indicated in FIG. 3 in that the expanded polymeric material is separated from the non-expanded polymeric material by a boundary surface 21 that is only shown dot-dashed. Since the wall 45 is not expanded, it has an acoustic impedance that is noticeably higher than that of the expanded polymeric material 43 as a consequence of the lack of gas enclosed in pores. Since, moreover, the thickness of the wall 45 is small in comparison to the wavelength of the pressure pulses in the non-expanded polymeric material, a negative reflection factor is present at the boundary surface 21. Pressure pulses incident in the reflector 42 are thus reflected as rarefaction pulses.

The wall 45 composed of the non-expanded polymeric material can be manufactured, for example, by first manufacturing a reflector blank composed entirely of expanded polymeric material having the conical inside contour indicated with a dotted line in FIG. 3. Proceeding from this blank, the reflector 42 is produced by pressing a heated paraboloid die into the reflector 42, giving the latter its ultimate inside contour. Due to the influence of heat, the expanded polymeric material 42 is thereby melted and is compressed under the influence of pressure to form the preferably gas-tight and liquid-tight wall 45, losing its foamed structure. The reflector 42 is subsequently provided with the plastic foil 44 at its remaining surface.

If the reflector 42 is produced in such a way that the creation of a foam structure is prevented from the very outset in the region of the wall 45, creation of the foam structure can be suppressed at the remaining parts of the surface of the reflector 42 as well, yielding the advantage that coating of the reflector with the plastic foil 44 can then be omitted.

Figure 4:
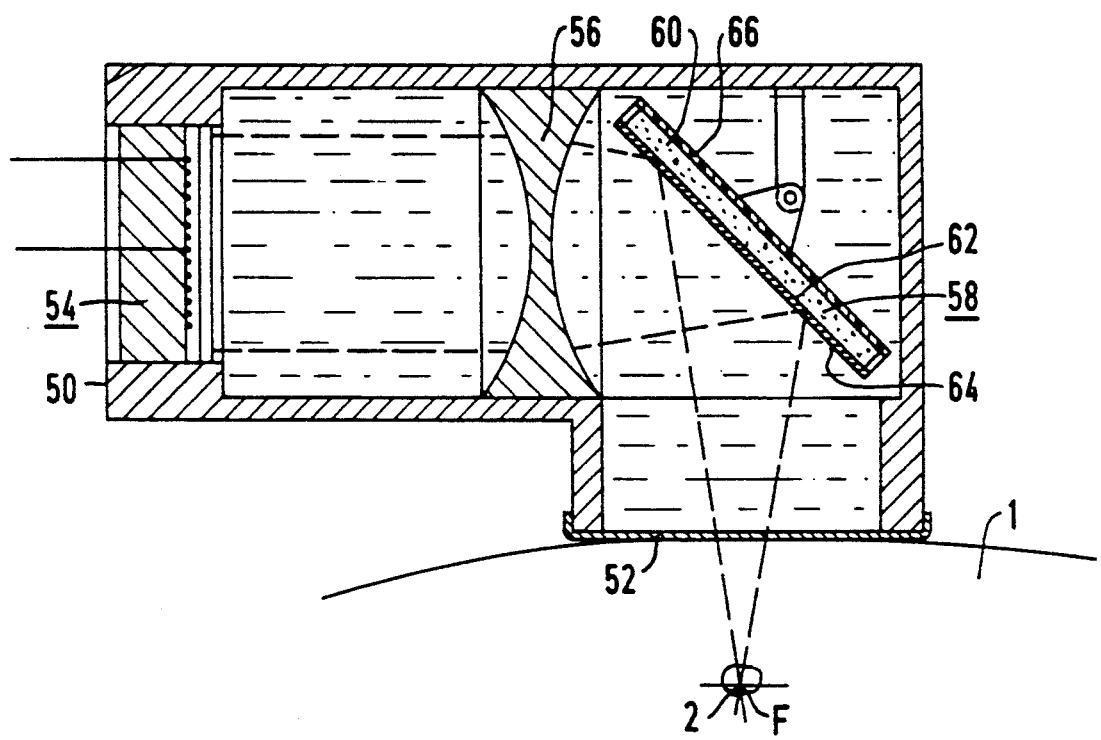
FIG. 4 is a schematic illustration of a longitudinal section of a further embodiment of a generator constructed in accordance with the principles of the present invention.

FIG. 4 shows a generator of the invention that has a tubular housing 50 angled by 90°, this housing 50 having one end closed by a flexible bellows 52 that serves the purpose of applying the generator to the body 1 of a patient. A pressure pulse source 54 is introduced into the other end of the housing 50. This can be a pressure pulse source as disclosed in U.S. Pat. No. 4,697,588 whose content is incorporated herein. The pressure pulse source 54 generates planar pressure pulses which are in need of focusing in order, for example, to be able to irradiate a pathological tissue modification 2. To this end, an acoustic positive lens 56 is introduced into that section of the housing 50 adjoining the pressure pulse source 54. The focused pressure pulses emerging from the positive lens 56 impinge a planar reflector 58 having a negative reflection factor that is arranged in the region of the bend of the housing 50. This reflector 58 reflects the incident pressure pulses as rarefaction pulses and deflects them by an angle of approximately 90°, so that the focused rarefaction pulses can be introduced into the body of the patient 1 through the bellows 52. The body of the patient 1 is arranged relative to the generator so that the pathological tissue modification to be treated is situated in the focus zone F of the rarefaction pulses.

As the acoustically soft medium, the reflector 58 has expanded polymeric material 60 with a planar, smooth boundary surface 62 facing toward the acoustic positive lens 56. The boundary surface 62 is separated from the water provided in the housing 50 as the acoustic propagation medium, by a metal foil 64 glued to the expanded polymeric material 60. At its remaining surface, the expanded polymeric material 60 is surrounded by an encapsulation 66 of plastic so that the metal foil 64 and the encapsulation 66 surround the expanded polymeric material liquid-tight. The thickness of the metal foil 64 is small in comparison to the wavelength of the pressure pulses incident on the reflector 58, so that these pressure pulses are essentially reflected only at the boundary surface 62.

The respective exemplary embodiments have in common that a wall 23, 26, 45 or 64 separating the respective boundary surface 21 or 62 of the acoustically soft medium 22, 43 or 60 from the liquid acoustic propagation medium, as well as supplementary measures potentially required (rings 24 or 25, plastic foil 44, housing 50) insure against penetration of the acoustic propagation medium into the acoustically soft medium 22, 43 or 60 and thus a premature failure of the generator for that reason is not possible.

A pressure pulse source having a cylindrical emission face for the pressure pulses and a reflector having a focusing, parabolic reflector face, or a pressure pulse source having a planar emission face, special focusing means (acoustic positive lens) and a planar reflector face are provided in the exemplary embodiments. The invention, however, can also be employed in generators that have differently fashioned emission faces, reflector faces or focusing means.

In the described exemplary embodiments, the generator of the invention is employed for treating pathological tissue modifications, however, it can also be utilized for other purposes.

Although modifications and charges may be suggested by those skilled in the art, it is the intention of the inventors to embody within the patent warranted hereon all changes and modifications as reasonably and properly come within the scope of their contribution to the art.

We claim as our invention:

1. A medical therapy apparatus for generating rarefaction pulses comprising:
   a housing;
   means for generating shockwave pulses disposed in said housing;
   reflector means, disposed in said housing spaced from said means for generating shockwave pulses, having a negative reflection factor for converting said shockwave pulses into rarefaction pulses;
   an acoustic propagation medium filling the space in said housing between said means for generating shockwave pulses and said reflector means; and
   said reflector means containing an acoustically soft medium having a boundary surface at which reflection of said shockwave pulses occurs facing said acoustic propagation medium and said means for generating shockwave pulses, said acoustically soft medium being acoustically soft relative to said acoustic propagation medium, and said reflector means having a wall consisting of material impenetrable by said acoustic propagation medium, said wall disposed between said acoustic propagation medium and said boundary surface of said acoustically soft medium.

2. An apparatus as claimed in claim 1 wherein said acoustically soft medium is a gaseous medium.

3. An apparatus as claimed in claim 1 wherein said acoustically soft medium consists of expanded polymeric material.

4. An apparatus as claimed in claim 1 wherein said wall consists of a material having an acoustic impedance substantially corresponding to the acoustic impedance of the acoustic propagation medium.

5. An apparatus as claimed in claim 1 wherein said means for generating shockwave pulses generates said shockwave pulses in a propagation direction and having a wavelength, and wherein said wall consists of material which is acoustically hard in comparison to said acoustic propagation medium and wherein said wall has a thickness in said propagation direction which is small in comparison to the wavelength of the shockwave pulses in said material of said wall.

6. An apparatus as claimed in claim 1 wherein said acoustically soft medium consists of expanded polymeric material and wherein said wall is joined to said boundary surface and is sealed thereto liquid-tight.

7. An apparatus as claimed in claim 1 wherein said means for generating shockwave pulses generates said shockwave pulses in a propagation direction and having a wavelength, and wherein said acoustically soft medium consists of expanded polymeric material, and wherein said wall is formed by a non-expanded layer of said polymeric material, said layer having a thickness in said propagation direction which is small in comparison to the wavelength of said shockwave pulses in said non-expanded layer of said polymeric material.

8. An apparatus as claimed in claim 7 wherein said non-expanded layer is joined with said expanded polymeric material in a one-piece component.

9. An apparatus as claimed in claim 1 further comprising:
focusing means, for focusing said shockwave pulses, disposed in said housing between said means for generating shockwave pulses and said reflector means.

10. An apparatus as claimed in claim 1 wherein said boundary surface has a shape which focuses said shockwave pulses.

11. An apparatus for generating rarefaction pulses comprising:
a housing;
means disposed in said housing for generating shockwave pulses in a propagation direction and having a wavelength;
reflector means, spaced in said housing from said means for generating shockwave pulses, having a negative reflection factor for converting said shockwave pulses into rarefaction pulses;
an acoustic propagation medium filling the space in said housing between said means for generating shockwave pulses and said reflector means;
said reflector means containing an acoustically soft medium at which reflection of said shockwave pulses occurs having a boundary surface facing said acoustic propagation medium and said means for generating pressure pulses, said acoustically soft medium being acoustically soft relative to said acoustic propagation medium; and
means disposed between said boundary surface of said acoustically soft medium and said acoustic propagation medium for separating said boundary surface from said acoustic propagation medium, consisting of material impenetrable by said acoustic propagation medium and which is acoustically hard in comparison to said acoustic propagation medium and which has a thickness which is small in comparison to the wavelength of said shockwave pulses in said material of said means for separating.

12. An apparatus for generating rarefaction pulses comprising:
a housing;
means disposed in said housing for generating shockwave pulses in a propagation direction and having a wavelength;
an acoustic propagation medium disposed in said housing in contact with said means for generating shockwave pulses and following said means for generating shockwave pulses in said propagation direction; and
reflector means, disposed in said housing spaced from said means for generating shockwave pulses and in contact with said acoustic propagation medium, having a negative reflection factor for converting said shockwave pulses into rarefaction pulses, said reflector means being a one-piece component consisting of expanded polymeric material having a boundary surface at which reflection of said shockwave pulses occurs and a layer of non-expanded polymeric material, said layer of non-expanded polymeric material being acoustically hard in comparison to said acoustic propagation medium and having a thickness in said propagation direction which is small in comparison to the wavelength of said shockwave pulses in said layer of non-expanded polymeric material, said layer of non-expanded polymeric material being disposed between said boundary surface and said acoustic propagation medium and being impenetrable by said acoustic propagation medium.

13. An apparatus as claimed in claim 12 wherein said boundary surface has a shape for focusing said shockwave pulses.

* * * * *